US009167965B2

(12) United States Patent
Jaeken et al.

(10) Patent No.: US 9,167,965 B2
(45) Date of Patent: Oct. 27, 2015

(54) INSTRUMENT FOR RAPID MEASUREMENT OF THE OPTICAL PROPERTIES OF THE EYE IN THE ENTIRE FIELD OF VISION

(75) Inventors: Bart Jaeken, Murcia (ES); Pablo Artal Soriano, Murcia (ES)

(73) Assignee: UNIVERSIDAD DE MURCIA, Murcia (ES)

( * ) Notice: Subject to any disclaimer, the term of this patent is extended or adjusted under 35 U.S.C. 154(b) by 159 days.

(21) Appl. No.: 13/823,121

(22) PCT Filed: Sep. 13, 2011

(86) PCT No.: PCT/ES2011/070640
§ 371 (c)(1),
(2), (4) Date: Jun. 19, 2013

(87) PCT Pub. No.: WO2012/049343
PCT Pub. Date: Apr. 19, 2012

(65) Prior Publication Data
US 2013/0265544 A1    Oct. 10, 2013

(30) Foreign Application Priority Data
Oct. 15, 2010  (ES) .................................. 201031526

(51) Int. Cl.
*A61B 3/10*    (2006.01)
*A61B 3/14*    (2006.01)
(Continued)

(52) U.S. Cl.
CPC ............... *A61B 3/103* (2013.01); *A61B 3/1015* (2013.01); *A61B 3/0008* (2013.01); *A61B 3/0083* (2013.01)

(58) Field of Classification Search
CPC ...... A61B 3/0083; A61B 3/103; A61B 3/107; A61B 3/12; A61B 3/1015; A61B 19/22; A61B 19/2203; A61B 19/5212; A61B 19/5225
USPC ......... 351/205, 208, 210, 211, 214, 221, 245; 606/4, 16
See application file for complete search history.

(56) References Cited

U.S. PATENT DOCUMENTS 3,485,090 A * 12/1969 Neumann .......................... 73/81
4,490,022 A * 12/1984 Reynolds ...................... 351/211
(Continued)

FOREIGN PATENT DOCUMENTS

EP        0 129 559 A1    1/1985
WO     WO 84/02533 A1    7/1984
WO     WO 2010/125394 A1  11/2010

OTHER PUBLICATIONS

International Search Report and Written Opinion issued Feb. 13, 2012 in PCT/ES2011/070640 with English language translation.
(Continued)

*Primary Examiner* — Scott J Sugarman
*Assistant Examiner* — Collin X Beatty
(74) *Attorney, Agent, or Firm* — Oblon, McClelland, Maier & Neustadt, L.L.P.

(57) ABSTRACT

An instrument measuring optical properties of an eye in an entire field of vision, including refraction and aberrations, including: a frame mounted on an ophthalmologic table that can be oriented in three perpendicular directions X, Y, Z; a support surface for a head of the subject; a hot mirror; a long mirror; an illumination sub-assembly including a fiber optic head; a lens; a diaphragm; a beam splitter; and a measurement sub-assembly with two lens and two mirrors; a camera including a matrix of micro-lenses on the inlet of camera, the camera being placed on the focal plane of the micro-lenses; the frame including a motor, a shaft of which rotates in the Y direction, to which an arm is attached that can rotate on the shaft; components of the illumination sub-assembly, components of a measurement sub-assembly, and the camera with the matrix of micro-lenses being mounted on the arm.

8 Claims, 3 Drawing Sheets

(51) Int. Cl.
*A61B 3/103* (2006.01)
*A61B 3/00* (2006.01)

(56) References Cited

U.S. PATENT DOCUMENTS

| | | | |
|---|---|---|---|
| 4,588,690 A | 5/1986 | Nissen et al. | |
| 4,699,482 A * | 10/1987 | Utsugi | 351/206 |
| 4,756,613 A * | 7/1988 | Okashita | 351/206 |
| 5,120,122 A * | 6/1992 | McAdams | 351/206 |
| 5,220,361 A * | 6/1993 | Lehmer et al. | 351/226 |
| 5,227,818 A * | 7/1993 | El Hage | 351/212 |
| 5,374,967 A * | 12/1994 | Hideshima et al. | 351/208 |
| 5,459,536 A * | 10/1995 | Shalon et al. | 351/226 |
| 5,491,757 A * | 2/1996 | Lehmer et al. | 382/128 |
| 5,926,252 A * | 7/1999 | Reyburn | 351/214 |
| 5,943,116 A * | 8/1999 | Zeimer | 351/221 |
| 6,361,167 B1 | 3/2002 | Su et al. | 351/206 |
| 6,460,997 B1 * | 10/2002 | Frey et al. | 351/211 |
| 6,474,815 B1 * | 11/2002 | Ulbers et al. | 351/214 |
| 7,575,322 B2 * | 8/2009 | Somani | 351/208 |
| 8,348,429 B2 * | 1/2013 | Walsh et al. | 351/210 |
| 2001/0055095 A1 * | 12/2001 | D'Souza et al. | 351/212 |
| 2003/0058403 A1 * | 3/2003 | Lai et al. | 351/212 |
| 2004/0044333 A1 * | 3/2004 | Sugiura | 606/4 |
| 2005/0105049 A1 * | 5/2005 | Maeda | 351/208 |
| 2007/0030446 A1 * | 2/2007 | Su et al. | 351/205 |
| 2007/0182927 A1 * | 8/2007 | Rathjen | 351/211 |
| 2007/0291229 A1 * | 12/2007 | Yamaguchi et al. | 351/221 |
| 2009/0303439 A1 * | 12/2009 | Kawai | 351/211 |
| 2012/0133888 A1 * | 5/2012 | Gray et al. | 351/206 |

OTHER PUBLICATIONS

International Preliminary Report on Patentability issued Oct. 17, 2012 in PCT/ES2011/070640 submitting English translation only.

Xin Wei, et al., "Design and validation of a scanning Shack Hartmann aberrometer for measurements of the eye over a wide field of view", Optics Express, vol. 18, No. 2, Jan. 2010, pp. 1134-1143.

Pedro M. Prieto, et al., "Analysis of the performance of the Hartmann-Shack sensor in the human eye", J. Opt. Soc. Am. A, vol. 17, No. 8, Aug. 2000, pp. 1388-1398.

Linda Lundström, PhD, et al., "Vision Evaluation of Eccentric Refractive Correction", Optometry and Vision Science, vol. 84, No. 11, Nov. 2007, pp. 1046-1052.

P. M. Prieto, et al., "Measurement of the Ocular Aberrations with a Hartmann-Shack Sensor: Evaluation of Performance and Limitations", IOVS, vol. 39, No. 4, Mar. 15, 1998, p. S396.

Juan Tabernero, et al., "Fast scanning photoretinoscope for measuring peripheral refraction as a function of accommodation", Journal of the Optical Society of America. A, Optics, image science and vision, NLM19798401, vol. 26, No. 10, Oct. 2009, 1 page.

R Daniel Ferguson, et al., "Adaptive optics scanning laser ophthalmoscope with integrated wide-field retinal imaging and tracking", Journal of the Optical Society of America. A, Optics, image science and vision, NLM21045887, vol. 27, No. 11, Nov. 1, 2010, 1 page.

* cited by examiner

INSTRUMENT FOR RAPID MEASUREMENT OF THE OPTICAL PROPERTIES OF THE EYE IN THE ENTIRE FIELD OF VISION

FIELD OF THE INVENTION

The present invention refers to an instrument for measuring optical properties, refraction and aberrations of the eye in the entire field of vision, especially for application for prescriptions of new systems of correction, such as eye glasses or contact lenses, that can control myopia in children and adolescents.

BACKGROUND OF THE INVENTION

Nowadays, the interest in the quality of the peripheral vision of the human eye (that is, what occurs outside the central zone where details are seen clearly) is greater than ever. This interest began in the 70's with the suggestion that peripheral vision could be an important factor that influences the progression of myopia (see, for example, the publication of F. Rempt, J. Hoogerheide, and W. P. H. Hoogenboom, "Peripheral Retinoscopy and Skiagram", Ophthalmologica 162, 1-10 (1971), or the publication of J. Hoogerheide, F. Rempt, and W. P. H. Hoogenboom, "Acquired Myopia in Young Pilots", Ophthalmologica 163, 209-215 (1971)).

To investigate said suggestion, several laboratories conducted tests with animals, as can observed in the following publications:

- F. Schaeffel, A. Glasser and H. C. Howland, "Accommodation, refractive error and eye growth in chickens", Vision Res. 28, 639-657 (1988).
- S. Diether and F. Schaeffel, "Local changes in Eye Growth induced by Imposed Local Refractive Error despite Active Accommodation", Vision Res. 37, 659-668 (1997).
- E. L. Smith, C. Kee, R. Ramamirham, Y. Qiao-Grider and L. Hung, "Peripheral Vision Can Influence Eye Growth and Refractive Development in Infant Monkeys", Invest. Ophthalmol. Vis. Sci. 46, 3965-3972 (2005).
- E. L. Smith, R. Ramamirtham, Y. Qiao-Grider, L. Hung, J. Huang, C. Kee, D. Coats and E. Paysse, "Effects of Foveal Ablation on Emmetropization and Form-Deprivation Myopia", Investigative Opthalmology & Visual Science 48, 3914-3922 (2007). D. O. Mutti, R. I. Sholtz, N. E. Friedman and K. Zadnik, "Peripheral Refraction and Ocular Shape in Children", Investigative Opthalmology & Visual Science 41, 1022-1030 (2000).

The importance of peripheral vision in the progression of myopia has been reproduced in tests involving primates and other animals. With regard to experiments carried out on the human eye, several research groups have found correlations that may indicate that an eye that has relatively more hypermetropia in the peripheral retina than in the fovea has a greater likelihood of developing myopia, in accordance with the following publications:

- A. Seidemann, F. Schaeffel, A. Guirao, N. Lopez-Gil and P. Artal, "Peripheral refractive errors in myopic, emmetropic, and hyperopic young subjects", J. Opt. Soc. Am. A 19, 2363-2373 (2002).
- J. Wallman and J. Winawer, "Homeostasis of Eye Growth and the Question of Myopia", Neuron 43, 447-468 (2004).
- D. A. Atchison, N. Pritchard, K. L. Schmid, D. H. Scott, C. E. Jones and J. M. Pope, "Shape of the Retinal Surface in Emmetropia and Myopia", Investigative Opthalmology & Visual Science 46, 2698-2707 (2005).
- D. O. Mutti, J. R. Hayes, G. L. Mitchell, L. A. Jones, M. L. Moeschberger, S. A. Gotter, R. N. Kleinstein, R. E. Manny, J. D. Twelker and K. Zadnik, "Refractive Error, Axial Length, and Relative Peripheral Refractive Error before and after the Onset of Myopia", Investigative Opthalmology & Visual Science 48, 2510-2519 (2007).
- L. Lundström, A. Mira-Agudelo and P. Artal, "Peripheral optical errors and their change with accommodation differ between emmetropic and myopic eyes", Journal of Vision 9(6):17, 1-11 (2009).
- X. Chen, P. Sankaridurg, L. Donovan, Z. Lin, L. Li, A. Martinez, B. Holden and J. Ge, "Characteristics of peripheral refractive errors of myopic and non-myopic Chinese eyes", Vision Res. 50, 31-35 (2010).
- W. N. Charman, H. Radhakrishnan, "Peripheral refraction and the development of refractive error: a review", Ophtal. Physiol. Opt. 30, 321-338 (2010).

Due to hypermetropia in the peripheral retina, the image is focused behind the retina. To obtain a focused image, the peripheral retina of the eye grows in order to compensate it, while at the same time it pushes the central retina back producing myopia. The first study with children who wear classes developed specifically for eliminating hypermetropia on the peripheral retina with the aim of preventing the progression of myopia corresponds to the publication by P. R. Sankaridurg, L. Donovan, S. Varnas, X. Chen, Z. Lin, S. Fisher, A. Ho, J. Ge, E. Smith and B. A. Holden, "Progression of Myopia With Spectacle Lenses Designed to Reduce Relative Peripheral Hyperopia: 12 Months Results", ARVO 2010 abstract, program # 2206.

Spanish patent application 200900692 referred to a "Device for Asymmetrical Refractive Optical Correction in the Peripheral Retina for Controlling the Progression of Myopia", develops another version of these devices for prophylaxis and prevention of myopia in children and/or adolescents. In effect, the optical device is a modifier of the peripheral retina of the eye for prophylaxis of the progression of myopia, consisting of a lens that in its inferior nasal quadrant progressively modifies the strength of the lens. The rest of the quadrants of the device present a graduated glass or flat glass configuration, depending on whether the user has a visual defect that requires optical correction or lacks said defect, respectively. The lens can either be an optical lens, a contact lens, or electro-optic systems.

Currently, the most used technique for measuring ocular aberrations is based on the so called Hartmann-Shack wavefront sensor. Said method is employed in many research laboratories throughout the world, and is also the most frequently used in commercially available systems. It consists in a micro-lens matrix that is optically conjugated with the pupil of the eye, and a camera placed on the focal plane of the micro-lenses. If a flat wavefront reaches the sensor, the camera registers a perfectly regular point distribution, whereas if the wavefront is deformed (that is, it has aberrations) the point distribution will be irregular. Mathematically, the displacement of each point is directly proportional to the derivative of the wavefront from each micro-lens. Wave aberrations are calculated from the images of the points.

To correctly investigate the impact of peripheral vision it is important to have instruments available that are capable of measuring it rapidly and with the necessary precision. Previously, instruments developed for measuring the refraction and/or aberrations of the central vision (on the fovea) were used. The only difference is that they require the subject to look at different angles in sequence while the fixed instrument takes the measurements. The measurements require a good deal of time (several minutes) and in order to shorten the time, the number of angles is reduced, which results in poor angular resolution. Furthermore, there are questions about whether rotating the eye changes the aberrations due to the tension of the eye muscles on the optics of the eye.

There is a demand for instruments that explore all eye angles so as to improve the measurements. The main difference between a static system and a scanning system is that in the first the subject needs to change his line of sight, whereas in the second, it is the instrument that changes it position to measure other angles.

There are two known instruments that perform a scan for measuring peripheral optical quality of the eye. The "peripheral photorefractor", in the document of J. Tabernero and F. Schaeffel, *"Fast scanning photoretinoscope for measuring peripheral refraction as a function of accommodation"*, J. Opt. Soc. Am. A. 26, 2206-2210 (2009), is a system that only measures eye refraction on one meridian of the pupil. The instrument moves in a linear translation while rotating a beam splitter. It has a 90° scanning range. The advantages of the system are that it has a large scan field and that the alignment of the subject is less critical; however, it has several important drawbacks. The operating base of the method is empirical, and the calibration of the reflection of the light off the back of the eye is essential for obtaining correct results. Also, only the refraction from one meridian can be measured. That is, it provides very partial measurements of the peripheral optics of the eye. Moreover, due to its design, a mirror moves in front of the subject, a situation that could give rise to errors when used on subjects who lack experience, as they will tend to follow it during the measurement.

The other scanner, disclosed in the document of X. Wei and L. Thibos, *"Design and validation of a scanning Shack Hartmann aberrometer for measurements of the eye over a wide field of view"*, Optics express 18, 1134-1143 (2010), measures aberrations of the eyes with the Hartmann-Shack (HS) technique. As mentioned above, this technique measures the wavefront that leaves the eye (see the documents of J. Liang, B. Grimm, S. Goelz and J. F. Bille, *"Objective measurement of wave aberrations of the human eye with the use of a Hartmann-Shack wave-front sensor"*, J. Opt. Soc. Am. A 7, 1949-1957 (1994); P. M. Prieto, F. Vargas-Martin, S. Goelz, P. Artal, *"Analysis of the performance of the Hartmann-Shack sensor in the human eye"*, J. Opt. Soc. Am. A, 17, 1388-1398 (2000)). The advantages of the instrument are that the only moveable objects are two mirrors and that all of the aberrations are measured, as well as the refraction. The camp being measured is not only the nasal and temporal retina, but also the inferior and superior retina. The drawbacks are that the measurements have a very low density, as only a 30° field can be measured, which is too little to form a good idea of the peripheral vision. This system, which has already been published, covers a small field and is slow (it requires 8 seconds to measure 37 angles).

Consequently, there is a need to have an instrument at hand to measure optical properties of the eye, refraction and aberrations, which is quick, robust, precise, and simple, and which makes it possible to take measurements on a broad visual field.

SUMMARY OF THE INVENTION

Therefore, the object of the present invention is to provide an instrument for measuring the optical properties of the eye in the entire field of vision that resolves the mentioned drawbacks.

The present invention refers to a new instrument and a new manner of application of the technique, which can be applied to learn more about the contribution of peripheral vision to the progression of myopia, and also be used for personalizing prescriptions of new systems of eyeglasses for preventing myopia by controlling peripheral optics.

The invention provides an instrument for measuring the optical properties of the eye in the entire field of vision, including refraction and aberrations, which comprises a frame mounted on an ophthalmologic table that can be oriented in three perpendicular directions X, Y, Z, with the X, Z directions being on the same plane and the Y direction perpendicular to the plane of the directions X, Z, the frame having a support surface for the head of the subject on whose eyes the measurements are to be performed, a hot mirror and a long mirror united to the frame and placed in front of the head of the subject; the instrument further comprising an illumination sub-assembly consisting in a fibre optic head; a lens L1, a diaphragm D, a BS beam splitter, and a measurement sub-assembly with two lens L2 and L3, two mirrors M1 and M2, and a camera adapted with a matrix of micro-lenses on its inlet, in such a way that said camera is placed on the focal plane of the micro-lenses; wherein the frame has a motor mounted on it, the shaft of which rotates in the Y direction, to which an arm is attached that can rotate with said shaft; being the components of the illumination sub-assembly, the components of measurement sub-assembly and the camera with the matrix of micro-lenses mounted on said arm.

By means of this configuration with a rotating arm on which are mounted the illumination sub-assembly, the measurement sub-assembly and the camera with a matrix of micro-lenses the distance between the plane of the pupil of the eye of the subject on which the measurements are going to be taken and the components placed on said arm can be the same for all angles, the rotation axis being the same as the axis of the motor.

Another advantage of the invention is that the subject whose eye is going to be measured remains still, without having to change his line of sight.

Another advantage of the invention is that it enables the subject whose eye is going to be measured to remain stationary and comfortable, as it is possible to equip the instrument with a chin rest to support the chin.

Other features and advantages of the present invention will be disclosed in the detailed description that follows from an exemplary embodiment of its object in relation to the accompanying figures.

BRIEF DESCRIPTION OF THE DRAWINGS

The following will illustrate, in a non-limiting manner, the object of the invention, making reference to the accompanying figures, in which.

DETAILED DESCRIPTION OF THE INVENTION

Figure 1:
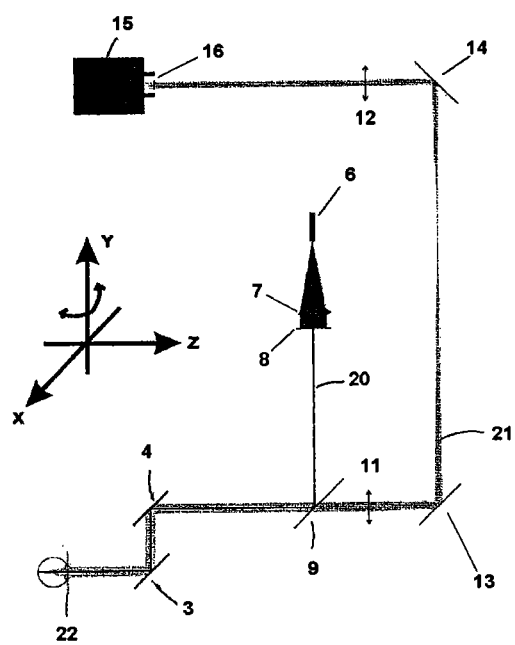
FIG. 1 shows a schematic view of the optical components of the instrument of the invention.
Figure 2:
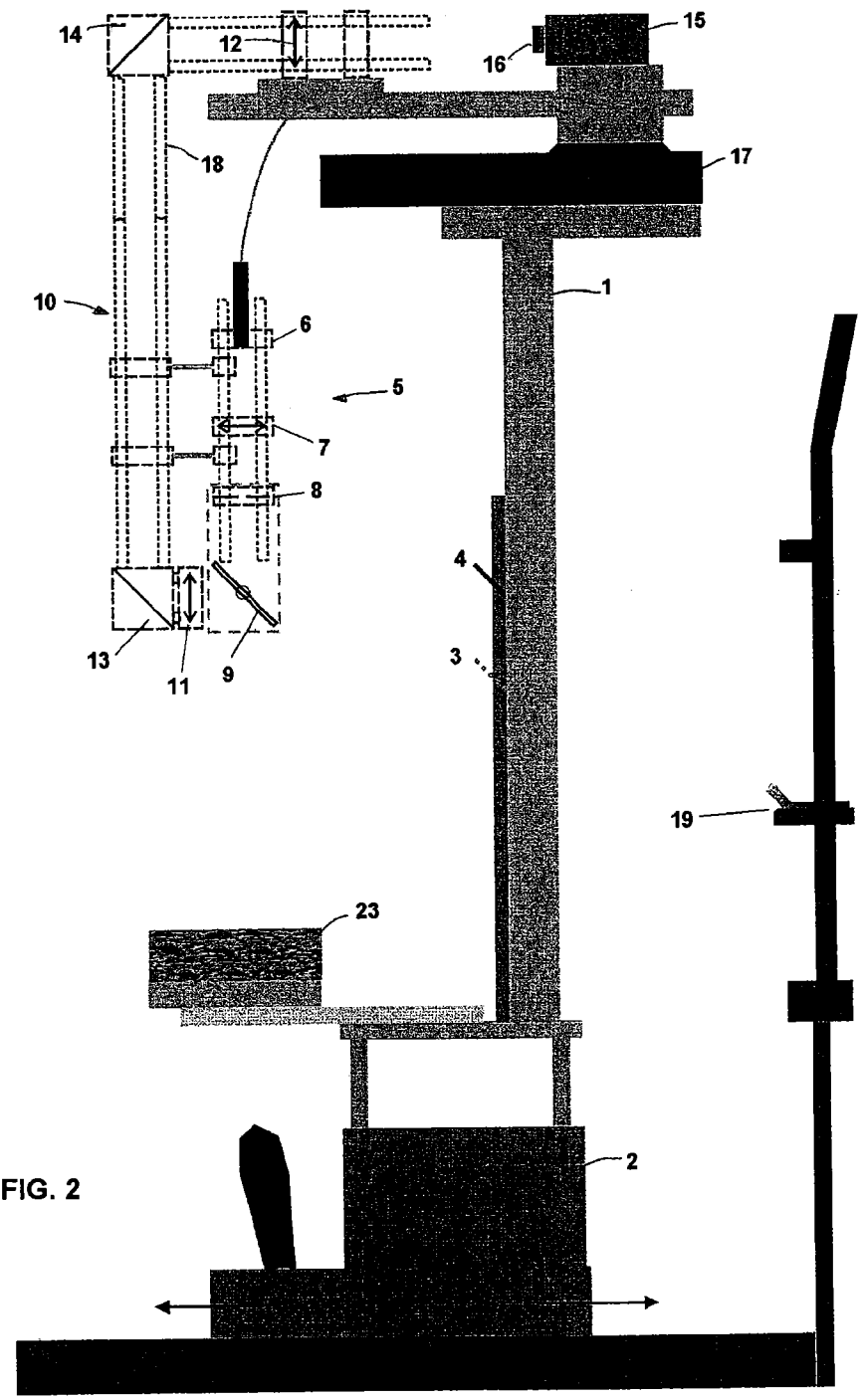
FIG. 2 shows a lateral view of the instrument of the invention with its components.
Figure 3:
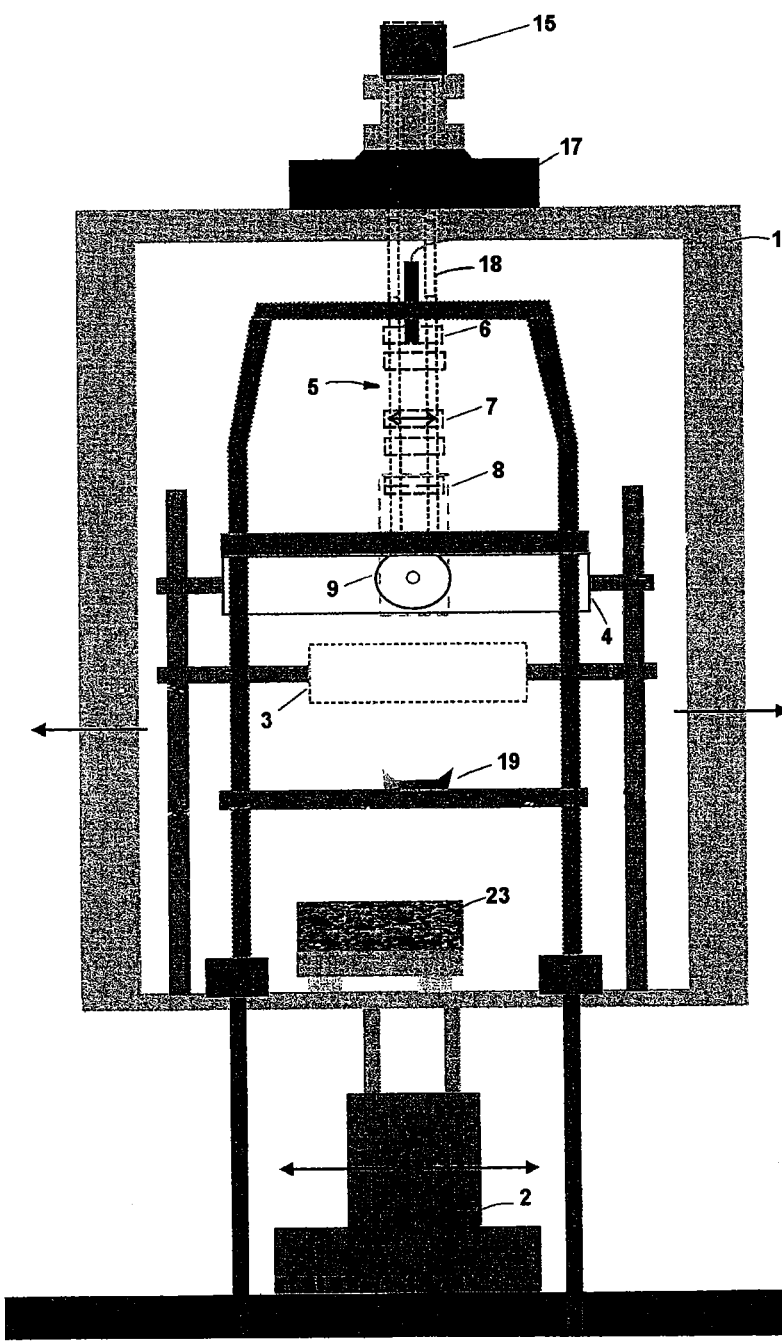
FIG. 3 shows a front view of the instrument of the invention with its components.

FIG. 1 shows schematically the optical components that constitute the instrument of the invention, and FIGS. 2 and 3 show the instrument of the invention with all of its components mounted.

As can be seen in said figures, the instrument comprises a frame 1 mounted on an ophthalmologic table 2, which can be oriented in three perpendicular directions X, Y, Z. Directions X, Z are on the same plane and direction Y is perpendicular to the plane of directions X, Z (see the axes system depicted in FIG. 2). The instrument has a support surface 19 for the head of the subject on whose eyes the measurements are going to be taken. Located in front of the head of the subject and united to frame 1 there is a hot mirror 3 and a long mirror 4.

The instrument also comprises an illumination sub-assembly 5 consisting of a fibre optic head 6; a lens 7 (L1), a diaphragm 8 (D), a beam splitter 9 (BS), and a measurement sub-assembly 10 with two lens 11 (L2) and 12 (L3), two mirrors 13 (M1) and 14 (M2), and a camera 15 with a matrix 16 of micro-lenses on the inlet of the camera 15, in such a way that said camera 15 is placed on the focal plane of the microlenses. Frame 1 has a motor 17 mounted on it (located on top of frame 1 in the embodiment of FIGS. 2 and 3), the shaft of which rotates in the Y direction, to which an arm 18 is attached that can rotate on said shaft. The components of illumination sub-assembly 5, the components of measurement sub-assembly 10 and the camera 15 with the matrix 16 of micro-lenses are mounted on said arm 18.

Input light 20 is depicted as a fine linear stroke and dark after fibre optic head 6, and output light 21 is depicted as a generally thicker linear stroke.

Motor 17 employed can be a direct current servomotor. Likewise, the movement of motor 17 can be governed by a controller for direct current servomotor.

The instrument can further comprise a laser pointer mounted on ophthalmologic table 2. The purpose of this element is to help the subject to stare at a point (in this case, the red point created by the laser pointer reflected on a surface located in front of the instrument).

Arm 18 which is attached to the shaft of motor 17 and on which are mounted the components of illumination sub-assembly 5, the components of measurement sub-assembly 10 and the camera 15 with a matrix 16 of micro-lenses, can be L-shaped. In FIG. 2 it can be seen that the components of illumination sub-assembly 5 and the components of the measurement sub-assembly 10 are located on the vertical arm; the horizontal arm making it possible to distance said components to the desired measurement with respect to frame 1 of the instrument.

Likewise, support surface 19 for the head of the subject on whose eyes the measurements are going to be taken, can consist in a chin rest with a curved concave central part, which makes it possible to restrain the head of the subject in a comfortable manner.

The design of the instrument has been centred on measuring a single visual meridian, although it could also be used in all of the directions of the retina. The horizontal meridian was chosen because in the studies carried out to date, it has been found that this meridian is the most likely to be related to the possibility of developing myopia. It has yet to be determined up to what angle the peripheral vision could be important. For this reason the biggest angle possible up to which the Hartmann-Shack technique (on which it is based) can function without problems is being sought. The limit is around 35° to 40° of the visual angle. At greater than 40°, the size of the smallest radius of the elliptic pupil is too small in many subjects. The instrument has been designed for scanning on a field of 90° and measuring the central 80° of the field of vision. The speed of the measurement is important for the precision of the results. There are several dynamic sources in the eye (accommodation, changes in the tear layer, and micro and macro saccadic movements) that can influence refraction and aberrations of the eye. To reduce the impact of these sources of error it is very important for the measurements to be taken rapidly (on the order of seconds). The duration of the measurements is also very important from the point of view of use of the instrument in clinical practice. An integral measurement (81 measurements on the horizontal meridian) takes 1.8 seconds. This makes it possible to measure the same eye several times in the same state. This allows taking an average which gives an even more precise result.

An angular resolution of an image per angle is chosen. The high resolution also improves the precision of the results. It is a known fact that the variation of aberrations changes at a low frequency, and it is likewise known that when sudden changes are measured it is very likely due to a corrupted image, which can be eliminated without losing much information.

The main difference between static measurements and scanned measurements has been explained above. When the subject does not need to change the direction of the eyesight between different measurements, measurement time can be reduced and the eye maintains the same muscle tension during all of the measurements. Given that the subject's comfort is very important for obtaining good measurements, our design uses a chin rest to hold the head and there are no components that move through the line on which the subject is staring.

For precise measuring it is important that the distance between the plane of pupil 22 of the eye (PP) and the HS sensor remains the same at all angles. For this reason, our instrument is based on a rotational movement so that each point of the circle is exactly the same distance from the centre. The point of rotation is the centre of motor 17. This point is translated to PP 22 of the eye with an L-shaped arm 18, which holds different optical components. Calculating the dimensions of the system is necessary to optimise different parameters. The radius of rotation is a function of the desired dimensions, angular scan range, reduction of the telescopic optic, system weight and use of standard optical and mechanical components.

Arm 18 L has two parts. An illumination part 5 and a measurement part. It is very important to ensure that the focal plane of L2 always coincides with PP 22 of the eye. It is mounted on a motor 17 which can rotate around the RY angle. Although it is not desirable to have moving components in the subject's field of vision, the design includes a large mirror 4 (LM) and a hot mirror 3 (HM). Both of these components are fixed. Given that hot mirror 3 is the only component placed in front of the eye of the subject, the subject has an open field of vision. FIG. 1 displays a scheme of the system.

A direct current servomotor governed by a controller can have speeds of 90°/s. A diode laser (whose light's wavelength is of 780 nm) connected to a fibre optic serves as a light source. The light enters the instrument at point F. D gives the possibility of adjusting the beam size between 1 mm for measuring and 12 mm for taking reference images. To reduce the size and weight of the system only one telescope (L2-L3) is used. ML is mounted on camera 15 using a type C mount. Camera 15 can have different technologies, sensor sizes and resolution times. In the case of the prototype developed to implement this invention, the camera has a 1024×768 pixel matrix with 8 bit resolution and can measure up to 117 images per second. Motor 17 functions with a USB cable and camera 15 through a standard Ethernet port, which makes it possible to use a standard computer. A specific support is designed to arrange all of the components of the instrument mounted on an ophthalmologic table 2 XYZ with chin rest. The table allows the instrument operator to align the instrument with the eye (right or left) of the subject without greatly bothering the subject by the side of the subject. FIGS. 2 and 3 show two views of the system.

The only non-standard optical component is long mirror 4 (220×35 mm). This component is necessary because of the desire to avoid having moving components in the line of sight of the subject. For staring, the subject needs to look at a red point created by a laser point on the wall in front of the instrument. The laser is attached to table XYZ and always indicates the correct position to stare at from any position of the table.

Aligning the instrument with the subject means putting the focal point of L2 in the centre of PP 22. Alignment follows a set and pre-established protocol. Two cameras are used. One shows the face/eyes of the subject. If the illuminating light does not enter the eye, the image of this camera can be seen, with a point on the face of the subject. Once the XY alignment is done, the system moves until reaching the position where the measuring beam enters the eye. Once the beam enters the eye, the HS camera begins registering images. The first alignment in direction Z is also done with the auxiliary camera. The system approaches until the cross drawn on the screen is superimposed on the pupil of the eye. To place the system in the correct position, arm 18 of the system moves up to 40°. When the HS image is in the same place as the image at 0°, the system is aligned. To ensure the measurements are always going to be correct, the system should also be placed at −40°. An experienced operator can align the instrument with the subject in about one minute.

Saving the images is completely automatic. A program is developed for controlling the instrument. The movement of motor 17 and the saving of the images with the HS camera are synchronized by means of the software. Recording speed is calculated to optimize different parameters, such as illumination intensity, maximum speed of motor 17, maximum speed of camera 15, sensibility of camera 15, and synchronization software limits. To reduce image saving time the measurements are done continuously. This method has the drawback that the optical quality is not measured from a single point, but rather the result of an integration over a small path that is run. To reduce the error, the integration path is never more than 50% of the distance between two measurements. For this reason all of the measurements are isolated. The error is also very small because the density of the measurements is higher than the variability of the optical aberrations being investigated, which means that integration is carried out on a field having equal values. The method yields other advantages, as there is no loss of resolution. Integration reduces the important problem of coherent speckling that normally damages images taken at high velocity and results in higher quality images for analysis and processing. Furthermore, given that the instrument can move without stopping, there are no image perturbations caused by vibrations of motor 17.

The standard system adjustments are detailed below: The system scans at a 90° angle. The images are only saved in the central zone of 80° so as to avoid perturbations of the images due to motor 17 stopping and starting. The illumination power is less than 10 µW, which is several orders of magnitude below the permitted exposure limits for this wavelength. Exposure time is 9 ms. The scanning is at 50°/s and the images are saved at 50 Hz. This means that an image is the integration of a path at a 0.45° visual angle and there is 0.55° of visible angle between the images. A measurement contains 81 HS images and saving it takes 1.8 seconds. Normally the measurement is repeated 4 times (324 HS images) and the result is the average. The total time is 7.2 seconds, which is still within the range in which the eye is at a constant state.

To determine optical aberrations based on HS images, a program was developed that combines different algorithms created to make the different phases of the elaboration. The first phase consists in detecting the points in the HS image. The second phase consists in comparing the position of the points by measuring against the perfect position. The difference between both is used to determine the aberration of the wave expressed as a series of Zernike polynomials. In the last phase the coefficients are rescaled to a circular pupil of 4 mm. The problem with elliptic pupils for measurements outside the axis is resolved by means of the enclosed circle method, as explained in the publication of L. Lundström, A. Mira-Agudela and P. Artal, *"Peripheral optical errors and their change with accommodation differ between emmetropic and myopic eyes"*, Journal of Vision 9 (6), 1-11 (2009). The refraction is calculated based on the second order coefficients.

As has been seen, the basic technique used in the instrument consists in an H-S sensor. The system is capable of measuring all of the aberrations and the refraction of the eye at an 80° angle within the field of vision with a resolution of 1 measurement per degree. In 1.8 seconds, 81 different angles can be measured. A new scanning method is used that makes rapid scanning possible over a wide angle of the retina. Given that from the mechanical point of view the method is optimized to take this type of measurements, it is possible to obtain a rapid, robust, precise and simple system.

With the instrument of the invention a rapid system for measuring the optical quality on the retinal periphery of the eye is achieved. Without movements of the subject, rapid and precise. The refraction and optical results can be used for prescribing eyeglasses to control myopia.

The same scanning principle could be applied to other systems of measurement of the optics of the eye besides Hartmann-Shack, as is proposed herein.

Although some embodiments of the invention have been described and depicted, it is obvious that modifications can be made to them within their scope, and that the invention should not be considered limited to said embodiments, but rather only to the content of the following claims.

The invention claimed is:

1. An instrument measuring optical properties of an eye in an entire field of vision, including refraction and aberrations, comprising:
    a support surface for a head of a subject on whose eyes measurements are to be performed, within a plane of a pupil of the eye;
    a frame mounted on an ophthalmologic table that can be oriented in three perpendicular directions X, Y, Z, with the X, Z directions being on a same plane and the Y direction being perpendicular to the plane of the directions X, Z, a hot mirror and a long mirror being united to the frame and placed in front of the head of the subject; and
    an optical assembly comprising an illumination sub-assembly including a fiber optic head, a lens, a diaphragm, a beam splitter, and a measurement sub-assembly including two lenses, two mirrors, and a camera including a matrix of micro-lenses on its inlet, the camera being placed on a focal plane of the micro-lenses,
    wherein the frame includes a motor mounted on it, a shaft of which rotates in the Y direction, to which an arm is attached that can rotate with the shaft, and such that a conjugated plane of the micro-lenses coincides with a rotation axis of the shaft, and
    wherein the optical assembly is mounted on the arm for rotational movement, the focal plane of at least one of the two lenses of the measurement sub-assembly coinciding with the plane of the pupil of the eye.

2. The instrument for measuring optical properties of an eye in an entire field of vision, in accordance with claim 1, wherein the motor is a direct current servomotor.

3. The instrument for measuring optical properties of an eye in an entire field of vision, in accordance with claim 2, wherein movement of the motor is governed by a direct current servomotor controller.

4. The instrument for measuring optical properties of an eye in an entire field of vision, in accordance with claim 1, further comprising a laser pointer mounted on the ophthalmologic table.

5. The instrument for measuring optical properties of an eye in an entire field of vision, in accordance with claim 1, wherein the arm that attaches to the shaft of the motor, on which are mounted the components of the illumination sub-assembly and the measurement sub-assembly, is L-shaped.

6. The instrument for measuring optical properties of an eye in an entire field of vision, in accordance with claim 1, wherein the support surface for the head of the subject on whose eyes the measurements are going to be taken includes a chin rest with a curved concave central part.

7. The instrument for measuring optical properties of an eye in an entire field of vision, in accordance with claim 1, wherein the motor and the camera are connected to a computer.

8. The instrument measuring optical properties of an eye in an entire field of vision, in accordance with claim 1, wherein the hot mirror is the only component placed in front of the eye of the subject, the subject thus having an open field of vision.

* * * * *